United States Patent
Plotkin et al.

(10) Patent No.: US 12,090,247 B2
(45) Date of Patent: Sep. 17, 2024

(54) WATER-SOLUBLE SEALANT COMPOSITION AND ITS PREPARATION

(71) Applicants: Alexander Plotkin, Tel Aviv (IL); Dmitri Menglet, Balaclava (AU)

(72) Inventors: Alexander Plotkin, Tel Aviv (IL); Dmitri Menglet, Balaclava (AU)

(*) Notice: Subject to any disclaimer, the term of this patent is extended or adjusted under 35 U.S.C. 154(b) by 900 days.

(21) Appl. No.: 17/157,502

(22) Filed: Jan. 25, 2021

(65) Prior Publication Data

US 2021/0154355 A1    May 27, 2021

Related U.S. Application Data

(63) Continuation-in-part of application No. 16/326,139, filed as application No. PCT/IL2017/050894 on Aug. 14, 2017, now Pat. No. 11,389,562.

(30) Foreign Application Priority Data

Sep. 12, 2016 (IL) .......................................... 247786

(51) Int. Cl.
*A61F 13/00* (2024.01)
*A61L 26/00* (2006.01)

(52) U.S. Cl.
CPC ....... *A61L 26/0004* (2013.01); *A61L 26/0014* (2013.01); *A61L 26/0047* (2013.01);
(Continued)

(58) Field of Classification Search
None
See application file for complete search history.

(56) References Cited

U.S. PATENT DOCUMENTS

| | | |
|---|---|---|
| 4,752,466 A | 6/1988 | Saferstein et al. |
| 5,185,001 A | 2/1993 | Galanakis et al. |

(Continued)

FOREIGN PATENT DOCUMENTS

| | | | | |
|---|---|---|---|---|
| CA | 2628836 C | * | 4/2011 | ........... A61K 9/5138 |
| EP | 0172710 | | 3/1992 | |

(Continued)

OTHER PUBLICATIONS

CA 2628836 C NPL Document (Year: 2011).*
(Continued)

*Primary Examiner* — Kim M Lewis
(74) *Attorney, Agent, or Firm* — Nath, Goldberg & Meyer; Joshua B. Goldberg

(57) ABSTRACT

A water-soluble sealant composition and a method for preparing the same which includes: adding soluble silver salt to a polyacrylic acid (PAA) solution; adjusting the pH of the PAA solution to 7-7.4; and heating the PAA solution to 90-125° C. The PAA has a molecular weight between 1000 to 8000. The composition includes a cross-linked poly (acrylic) silver matrix having affinity to proteins. The silver salt can be silver nitrate and/or silver acetate. The matrix may create hydrophilic zones which bind proteins. The composition when in contact with proteins may form hexagonal packing complexes of rod-like poly(acrylic) particles and proteins. It may form a clot made of multi-layered grid structure. In some cases, the complexes create loops that form cells comprising proteins e.g., albumin. The proteins may be of a body fluid such as blood, lymph and combinations thereof. The composition may be applied for a medical condition such as hemorrhage and lymphorrhea.

19 Claims, 11 Drawing Sheets

(52) U.S. Cl.
CPC ....... *A61L 26/0076* (2013.01); *A61L 26/0095* (2013.01); *A61L 2300/104* (2013.01); *A61L 2300/418* (2013.01); *A61L 2400/04* (2013.01)

(56) References Cited

U.S. PATENT DOCUMENTS

| | | | |
|---|---|---|---|
| 5,330,974 | A | 7/1994 | Pines et al. |
| 5,407,671 | A | 4/1995 | Heimburger et al. |
| 5,474,782 | A | 12/1995 | Winter et al. |
| 5,484,913 | A | 1/1996 | Reginald et al. |
| 5,692,302 | A | 12/1997 | Martin et al. |
| 5,800,372 | A | 1/1998 | Bell et al. |
| 5,874,479 | A | 2/1999 | Martin et al. |
| 5,981,606 | A | 11/1999 | Martin et al. |
| 6,454,787 | B1 | 9/2002 | Maddalo et al. |
| 6,521,265 | B1 | 2/2003 | Patterson et al. |
| 8,921,317 | B1 | 12/2014 | Burton et al. |
| 2003/0008011 | A1 | 1/2003 | Mershon |
| 2003/0176828 | A1 | 9/2003 | Buckman et al. |
| 2003/0181917 | A1 | 9/2003 | Gertner et al. |
| 2005/0137512 | A1 | 6/2005 | Campbell et al. |
| 2006/0088589 | A1 | 4/2006 | Gorman et al. |
| 2011/0066182 | A1 | 3/2011 | Falus et al. |
| 2011/0224592 | A1 | 9/2011 | Buckman et al. |
| 2012/0323155 | A1 | 12/2012 | Buckman et al. |
| 2013/0029030 | A1 | 1/2013 | Larsen |
| 2014/0034567 | A1 | 2/2014 | Swift et al. |
| 2015/0125513 | A1 | 5/2015 | McCarthy et al. |
| 2015/0224220 | A1 | 8/2015 | Olson et al. |
| 2015/0238652 | A1 | 8/2015 | Eutick |
| 2019/0184057 | A1 | 6/2019 | Plotkin et al. |

FOREIGN PATENT DOCUMENTS

| | | |
|---|---|---|
| EP | 2897688 | 7/2015 |
| JP | 2009235098 | 10/2009 |
| JP | 2013522246 | 6/2013 |
| RU | 2372944 | 7/2009 |
| WO | WO 01/41774 | 6/2001 |
| WO | WO 2006/044882 | 4/2006 |
| WO | WO 2007/068492 | 6/2007 |
| WO | WO 2008/063157 | 5/2008 |
| WO | WO 2011/113436 | 9/2011 |
| WO | WO 2014/043743 | 3/2014 |
| WO | WO 2014/071053 | 5/2014 |

OTHER PUBLICATIONS

Safin DA, Romanov DV, Silver poly (acrylate) matrix (Haemoblock) in children with lymphatic malformations, Journal of Pediatric Surgery Case Reports (2019).

Degovtsov, et al., "Using local hemostatic to prevent seromas in patients with large incisional hernias randomized controlled trial," The World Journal of Hernia and Abdominal Wall Surgery (2020).

Lukashik, et al., "The effect of the surgical hemostatic product "Hemoblock"TM on in vitro bacterial colonization," Clinical microbiology and antimicrobial chemotherapy, vol. 22 No. 1 (2020).

* cited by examiner

WATER-SOLUBLE SEALANT COMPOSITION AND ITS PREPARATION

CROSS-REFERENCE TO RELATED PATENT APPLICATIONS

This application is a continuation-in-part patent application of U.S. patent application Ser. No. 16/326,139 which is the U.S. national stage patent application of International Application No. PCT/IL2017/050894, entitled "Wound covering with haemostatic action and the method of its creation" which was filed on Aug. 14, 2017, and which claims priority to and the benefit of Israeli Patent Application No. 247786, entitled "Wound covering with haemostatic action and the method of its creation" filed on Sep. 12, 2016, the entire contents of each of which are incorporated herein by reference.

TECHNICAL FIELD

The present teachings relate to the field of medical emergencies and surgery. More particularly, the present teachings relate to medical conditions of hemorrhage and lymphorrhea.

BACKGROUND

Physical traumatic injury is a frequent cause of morbidity and mortality worldwide. Traffic and other accidents and crimes of violence are the largest portion of the emergency room admissions. Conflicts in conventional or unconventional warfare have become an ongoing reality around the world. In civilian communities or on the battlefield, the inability of first responders to control hemorrhage in many cases is a major contributor to the mortality rate. In combat, the vast majority of the deaths occur in the field before an injured person can be transported to a treatment facility. Similarly, almost 80% of civilian trauma fatalities are attributed to uncontrolled hemorrhage.

If blood vessels are injured by physical traumas including surgical interventions, bleeding will occur. If small bleedings are left alone they will eventually be arrested by a normally occurring physiological process characterized by a chain of events involving the combined activity of vascular, platelet, and plasma factors, leading to the formation of a blood clot.

A variety of methods are known to stop losses of blood or fluids and imitate defensive functions of intact tissue during heavy bleeding. Heavy bleeding may be stopped in many cases if large vessels can be flattened. This may be done by transfer of external pressure through adjacent tissue or bandaging material. Less severe injuries require surgical care, non-adhesive bandages such as the first aid bandages may limit minor hemorrhage and prevent wound contamination.

But in practice there are known, that heavy injuries and burns often exceed the capabilities of first aid bandages. Some injuries exceed the capabilities of all bandages and care, which are available at the site of injury. Victims frequently bleed to death before they can benefit from care by highly trained and superbly equipped surgeons who might save them. It is known that hemorrhage and infections or toxic effects consequent to contamination of open wounds is the cause of many battlefield deaths and increases the morbidity of surviving casualties.

There is known, that relatively minor injuries are often covered with sterile cotton gauze pads that are held over the injured site by pressure from an adhesive barrier strip affixed to adjacent normal skin. Such first aid bandages may be used to sequester small amounts of blood within the absorbent pad until components of blood and damaged tissue can form a fibrin-based clot. The clot initially clogs the ends of small blood vessels and adheres to wounded surfaces. When large vessels are cut or torn, the rapid flow of escaping blood tends to remove fibrin clots before they can clog the vessel and adhere to the adjacent damaged tissue.

Often in medical practice the blood adhering to damaged tissue is clotted and slowly transformed into a scab that serves as a tissue cover substitute. This scab retains body fluids while sealing out bacteria and other environmental hazards. Wound healing normally takes place under cover of the protective scab, which prevents drying of underlying cells and undesirable inflammatory reactions that limit normal healing. Such healing requires closure of any void with fibroblasts and the migration of epidermal cells over fibroblasts and fibroblastic collagen products under physiological conditions. There is a need for methods able to rapidly provide the protective functions normally provided by epithelial cells and to foster re-epithelialization for re-establishment of such functions. An artificial scab is expected to provide such immediate protection but it may also be used to prevent or retard possibly disfiguring scar.

There are known from the medical practice that major causes of death due to trauma are hemorrhage and neurological trauma with the rest being attributed to devastating multiple injuries. Even when the injured survives long enough to be transported to a medical facility, hemorrhage still remains the leading cause of late death and complications. Abdominal injuries pose a formidable problem, especially for children. Being the largest solid organs within the abdomen, the liver and the spleen are the most frequently injured organs and being very vascular are generally difficult organs to control bleeding. Massive bleeding from the liver is currently controlled by Pringle's maneuver or packing of the wound, both of which procedures require surgical intervention and cannot be applied on the battlefield or at the site of the accident. Spleen trauma can bleed profusely with minimal injury and attempts to control the bleeding are often inadequate.

Early and effective hemorrhage control can save more lives than any other measure. All current hemostatic agents for intracavitary bleeding are designed to be used in the operating room with the cavity wide open. In an emergency situation at the site of the accident or on the battlefield uncontrolled or poorly controlled hemorrhage is often lethal. Also, certain types of surgery such as laparoscopic procedures or brain surgery can be seriously complicated by internal bleeding that requires more effective and less invasive treatment.

Previous efforts have been made to find more effective ways to control bleeding and reduce the associated high mortality rates. One of such method was the local use of fibrin as a fibrin glue. Fibrin glue is composed of a mixture of human fibrinogen and bovine thrombin. It is sold as a kit containing separate vials of fibrinogen and thrombin solutions. These solutions are mixed together and applied to the wound in various ways, including as a paste, as a spray or on a patch. Fibrin glue, however, is an inconsistent and ineffective treatment for hemostasis. The mixing, soaking, and coating of a patch with fibrin glue requires time-consuming and cumbersome procedures during which further hemorrhaging can occur and the fibrin solutions can be washed away by intense bleeding. Examples of the continuing effort to find the right composition for fibrin glue can be found in some U.S. patents, such as described by Galanakis Dennis in U.S. Pat. No. 5,185,001; Pines Eli et al. in U.S. Pat. No. 5,330,974; Heimburger Norbert et al. in U.S. Pat. No. 5,407,671; Burton Robert in U.S. Pat. No. 8,921,317 and Swift Matthew et al. in the Pat. Application US2014034567 (A1).

Similarly, efforts have been made to provide an effective non-fibrin-based hemostasis treatment for topical use. Examples of such attempts to find an effective hemostatic composition as described by Maddalo Francis et al. in U.S. Pat. No. 6,454,787 and McCarthy Simon in Pat. Application US2015125513 (A1), both of which relate to methods for depositing thrombin in solution or powder onto a hemostatic device, such as a sponge that includes a collagen component. Safferstein Lowell et al. in U.S. Pat. No. 4,752,466 and Gertner Michael in Pat. Application US2003181917 (A1) described the thrombin aerosol means. In both these patents there were disclosed thrombin delivered systems in a dry powdered form from a valve-actuated pressurized propellant-containing aerosol containers.

Other hemostatic compositions and devices are directed to the problem of providing an effective hemostatic device, such as that disclosed by Falus George in the Pat. Application US2011066182 (A1) and PCT application WO2014071053 (A2), which focus on creating hemostatic fabrics that use collagen hemostatic fibers that can be pressed into a hemostatic fabric and are formed to specific anatomical contours. Those patent applications disclose a four part fibrin-based, polymeric cross-linked, surgical sealant and hemostatic agent wherein the cross-linking polymers create a matrix or foundation as a means of holding the hemostatic agent on the place against the site of bleeding. These and other recent efforts evidence that the goal of providing an effective, safe hemostatic device or composition that is capable of promoting fast clotting for surface and internal hemorrhaging is an ongoing need.

Those publications listed above are a small representation of the many and varied efforts that have been made in the past to provide a fast, effective hemostatic device or composition capable of field or emergency room use in the overall effort to save lives by controlling bleeding from injuries and wounds. Among the many possible hemostatic agents that are included in such compositions and products are: thrombin, fibrinogen, collagen, calcium ions, Arginine-Glycine-Aspartic Acid (RGD) peptide, protamine sulfate, epsilon amino-caproic acid, chitin, and others.

In addition, many of the compositions also include vary amounts and combinations of additional therapeutic agents and medicaments, such as agents that promote wound healing and/or reduce pain. Agents that promote wound healing and/or reduce pain include anti-inflammatory agents (steroidal and non-steroidal), such as agents that inhibit leukocyte migration into the area of surgical injury, anti-histamines, agents that inhibit free radical formation, and bacteriostatic or bactericidal agents.

Several patents disclose compositions that promote wound healing, for example, Eutick Malvin in Pat. Application US2015238652 (A1), WO2014043743 (A1) and EP 2897688 (A1). Other patents disclose compositions that promote wound healing in conjunction with a clotting component, including Martin Alain, U.S. Pat. Nos. 5,692,302; 5,874,479, and 5,981,606; Stillwell Reginald et al. in U.S. Pat. No. 5,484,913, and Winter Rudolf et al. in U.S. Pat. No. 5,474,782.

Dobrovolskaia Marina et al. in PCT Pat. Application WO2008063157 (A1), US Pat. Applications US 2012323155 (A1) and US 2011224592 (A1) disclose the devices and methods for achieving hemostasis of traumatized patients. Such haemostatic devices and methods are especially useful in the emergency, trauma surgery or military setting. The patients may have received trauma to abdominal viscera, the thoracic cavity or the periphery. The devices utilize fluid impermeable on outer surfaces and distribute pressure to achieve tamponade and hemostasis, primarily by exertion of pressure. These hemostatic devices may be placed and removed by open surgery or laparoscopic access without generating excessive re-bleeding, and may further comprise antimicrobial or thrombogenic regions.

A multitude of other patents, for example, Gorman Anne Jessica et al., in U.S. Pat. Application US2006088589 (A1), PCT Pat. Application WO2006044882 (A1), etc., disclosed various ready-to-use bandages, pads or other carrying agents containing hemostatic agents, including fibrin, thrombin, collagen, polyethylene oxide, Factor VIII, epsilon aminocaproic acid (EACA) with calcium chloride, etc. Sakamoto Izumi discloses in European Pat. Application EP0172710 (A2) a carrier in the shape of a flake or fiber having thrombin and Factor XIII affixed thereto.

Other patents disclose various fibers capable of inducing clotting. For example, Popov Vladislav A. et al in Russian Pat. RU2372944 (C2) disclosed a wound healing coating which contains a hydrophilic fabric base, a hydrogel layer containing acrylic acid and acrylamide with a coupling agent with the hydrogel layer having pH 7.0-7.5 and absorbability 36-44 g/g, a water-soluble biodegradable polymer containing mixed gelatin and poly-N-vinylpyrrolidone, and as biologically active components: fullerene C60, antimicrobic, necrolytic, antifermental and haemostatic agents in certain component relation in the coating, wt. %.

Buckman Robert F. et al. in U.S. Pat. Applications US2003176828 (A1) and US2012323155 (A1) disclose haemostatic packing devices and methods which are especially useful in the emergency, trauma surgery or military setting. The devices come in a variety of configurations including sheet, rolled sheet, folded sheet and polygonal solids including extruded shapes. The devices are capable of serving as carriers for thrombogenic or antipathogenic agents. Peripheral haemostatic packing devices include optional adhesive hemostatic barriers to cover the entire wound area over the hemostatic pack. The hemostatic packing devices may be placed and removed by open surgery or laparoscopic access without generating excessive re-bleeding, and may further comprise antimicrobial or thrombogenic regions.

Bell Eugene, et al., in U.S. Pat. No. 5,800,372, disclose a dressing made of microfibrillar collagen and a superabsorbent polymer for blood absorption and clotting inducement. Patterson James et al, in Japan Pat. Application JP2009235098 (A) and U.S. Pat. No. 6,521,265 disclosed an admixture of salt ferrate with a cation exchange material that, when hydrated results in the concentration of blood and reduction of $Fe^{+6}$ to $Fe^{+++}$ to induce clotting.

Mershon Millard Marsden in U.S. application US 20030008011(A1) disclosed acid forms of cross-linked polyacrylic acid with polyvinyl alcohol that forms a gel for stopping minor bleeding. Campbell Todd in U.S. Pat. Application US20050137512 (A1) disclosed a compressed sponge for hemorrhage control made by freeze drying from a composition of polyacrylic acid.

And finally, Kristian Larsen in some patent applications WO2011113436 (A1), US2013029030 (A1), JP2013522246 (A) and EP2547371 (A1) described a method for making the matrix material which has a pharmaceutical composition coated onto the surface of the matrix material using ultrasonic spray technology. In one specific embodiment these applications also described how to the use of this matrix material for promotion of hemostasis and/or wound healing.

As discussed above there are numerous widely varied hemostatic compositions in use. However, these conventional compositions share a common deficiency in their purpose to control bleeding and save lives. That shared deficiency is a speed of bleeding stop. It is therefore of critical importance for the safety of the trauma patient to whom a hemostatic composition or device has been administered by first providers is provision of quickly possible and effective hemostatic effect. It is a much-needed advancement in the field of emergency medicine and the surgical arts.

Thus, a proposed wound covering, blood clotting composition and method of its use solves the aforementioned problems as desired.

SUMMARY OF THE INVENTION

With the above circumstances and state of the art in mind, the inventors discovered new wound covering and a method for suppression of massive blood or fluid loss by inducing artificial clotting, based on water of blood or fluids, using compositions comprising anhydrous polymers such as polyacrylic acids of various chain lengths and modified monomer components.

The present invention lies within the area of biological tissue sealants and hemostats, which are biodegradable and nontoxic, intended for emergency, surgical and therapeutic use. An object of the present invention is a method for creation of wound covering with haemostatic action, which consists of certain steps. In the first step there is application to the open wound a grid-forming water-soluble haemostatic composition designated as a Hemoblok, which consists of a polyacrylic matrix as an active ingredient. This matrix comprises at least one polymeric carboxylic acid of a predetermined average molecular weight range, and a bactericidal agent. Further, there is created by Hemoblok on the wound surface a clot formation with the blood plasma proteins, including albumin. Then Hemoblok creates on the wound surface a polyacrylic matrix structure containing albumin molecules in the cells of the polyacrylic matrix (grid), which is the primary organizer of sustainable polyacrylic film. Further, Hemoblok is supplied on the open wound surface to form thereon multilayered solid polyacrylic film. Then the Hemoblok supplying on the wound surface is terminated with the following replacement of the surface structure hemoblok-protein by fibrin. On the last step the plasma formation of the polyacrylic matrix is implemented.

The polyacrylic matrix structure serves as a primary organizer of stable film on the surface of the wound and is kept therein by weak interaction of polyacrylate negatively charged ions (anions polyacrylate) with positively charged proteins' functional groups.

Further, silver ions are reduced by protein molecules to form a stable complex wherein polyacrylate anions form a strong communication with the positively charged proteins' functional groups and provide for protein agglutination on the wound surface whereas at the threshold of albumin >10 mg/liter the Hemoblok introduction gives a quick effect.

Further, there is created stable complex of the polyacrylic matrix structure forming multiple micro-layers, creating a solid polyacrylate film on the surface of the wound. Reduced metallic and polyionic silver in a complex with proteins is a powerful bactericidal factor that provides the lack of suppuration during using the Hemoblok. Further, surface structure hemoblok—protein is replaced by fibrin over time. The polyacrylic matrix plasmolysis is provided during the first day and provides ulcers transformation by fibrin on the second day.

An embodiment is also possible in which the polyacrylic matrix structure comprises polyacrylate silver in very small amounts, comparable to natural blood coagulation factors. In this case the polyacrylic matrix structure serves as the main organizer (plasticizer) of stable blood clot on the wound surface.

The polymeric carboxylic acid is a polymeric $\alpha,\beta$-unsaturated carboxylic acid, selected from the group consisting of poly (acrylic acid), poly (methacrylic acid) and poly (crotonic acid). The concentration of the polymeric carboxylic acid is from about 0.5% to about 5% by weight, preferably 1% by weight. The polyacrylic acid has the structural formula [CH2—CHCO2H]n, where n is at least about 14, preferably about 30. The polyacrylic matrix contains also the polyacrylic acid, which has the structural formula [CH2—CHCO2H]n, where n is from about 14 to about 1400, preferably from about 14 to about 140.

The bactericidal agent is selected from the group consisting of dissolved silver ions, oligomeric silver clusters, silver colloidal nanoparticles and any mixture thereof. The silver colloidal nanoparticles are in the size of from about 0.5 nm. to about 5 nm. and contains from about $1\times10-5$ moles per liter to about 1 mole per liter silver. A grid-forming water-soluble haemostatic composition designated as a Hemoblok has a pH between about 3 and about 10, preferably equal to human blood physiological pH. This grid-forming water-soluble haemostatic composition designated as a Hemoblok may be additionally supplied with the therapeutic substances incorporated in Hemoblok as soluble drugs to serve as antimicrobial agents, anti-inflammation agents, agents that resist apoptosis, or agents that preserve cellular functions. The antimicrobial agents are selected from the group consisting of antibiotics and sulfonamides. The anti-inflammation agents, the agents that resist apoptosis, and the agents that preserve cellular functions are selected from the group consisting of antioxidants and nutrients.

The grid-forming water-soluble haemostatic composition provides a protective layer that limits development of fibroblastic tissue and supports epithelialization. The grid-forming water-soluble haemostatic composition is present on or in a woven or non-woven fabric, which is selected from the group consisting of gauze, paper, plastics, silicone polymers, resorbable materials, latexes and suitable derivatives of thereof. The resorbable material is selected from the group consisting of proteinaceous materials, carbohydrate substances and resorbable suture materials. During mild bleeding on large wound surfaces such as burns, post-operative dressing a Hemoblok haemostatic composition may be used as a spray. A Hemoblok haemostatic composition in form of a spray is used during surgery processing of the wound surfaces, including abdominal operations on parenchymal organs, and postoperative procedures such as bandaging, wound treatment, cuts and seams treatment.

Another object of the present invention is a kit for creation of wound covering. The kit comprises packaged in association: a) a package with the grid-forming water-soluble haemostatic composition designated as a Hemoblok and consisting of a polyacrylic matrix as an active ingredient, where the matrix comprising at least one polymeric carboxylic acid of a predetermined average molecular weight range, and a bactericidal agent, all as is described above, and b) a dispenser for applying the hemoblok to open wounds, which is made of a woven or a non-woven fabric, a tube, a bandage impregnated with the hemoblok, or a container having at least one opening through which the hemoblok may be dispensed.

According to some aspects of the present teachings a method for preparing a water-soluble sealant composition includes:

adding soluble silver salt to a polyacrylic acid (PAA) solution;

adjusting the pH of the PAA solution to 7-7.4; and heating the PAA solution to 90-125° C.

The PAA has a molecular weight between 1000 to 8000. The composition includes a cross-linked poly(acrylic) silver matrix having affinity to proteins. The silver salt can be silver nitrate and/or silver acetate. The matrix may create hydrophilic zones which bind proteins. The composition when in contact with proteins may form hexagonal packing complexes of rod-like poly(acrylic) particles and proteins. It may form a clot made of multi-layered grid structure. In some cases the complexes create loops that form cells comprising proteins e.g., albumin. The proteins may be of a body fluid such as blood, lymph and combinations thereof.

In some examples the above method includes preparing the PAA solution. In some cases the method includes cooling to ambient temperature after said pH adjusting. Adjusting pH may be made with an alkali such as NaOH and/or KOH. Heating may be done above ambient pressure, e.g., 2 atmospheres absolute. In some examples heating may take for more than 30 minutes. In some cases the heating is for up to 40 minutes.

Composition according to some aspects of the teachings is prepared by the method. The composition may be applied for stopping leakage of body fluid, mainly, blood (hemorrhage), lymph (lymphorrhea) and combinations thereof.

DETAILED DESCRIPTION OF EMBODIMENTS

Figure 1:
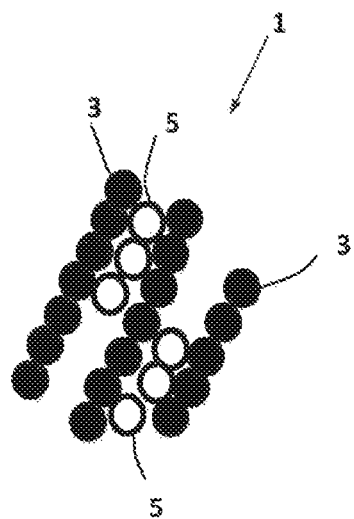
FIGS. 1 and 2 illustrate the rod-like particles of polyacrylic matrix which become centers of protein molecules binding and are adsorbed on the surface of the charged rod-like particles.

Embodiments of the present invention are disclosed herein below with a view of disclosing both the present invention and equivalents thereof which are within reach of a skilled person having read the present application.

In clinical practice, there are used different ways of influencing the source of the bleeding: diathermocoagulation, laser photocoagulation, cryotherapy, application of film-forming agents, irrigation and injection hemostatic solutions, and the introduction of vasoconstrictor and sclerosing agents. The subject of the present invention pertains to medical wound covering means and methods for stopping or decreasing the blood flow from an open wound or a medical or surgical procedure site.

According to the first embodiment of the present invention, the medical wound covering means is prepared on the basis of composition having combined antibacterial and haemostatic properties, which has storage stability and long shelf-life.

In the last twenty years the major objective of the research conducted by the present inventors has been to find a composition which includes a poly(acrylic) matrix and body proteins such as blood albumin. In one example it was revealed that the above composition which includes albumin molecules incorporated in the cells of the polyacrylic matrix, allows a formation of a sustainable grid structure of a clot film. It became apparent that the organized structure of the poly(acrylic) matrix possesses a much higher affinity to the plasma proteins, leading to a significant enhancement of creation of a hemostatic wound covering. Formation of a coordination manifold of silver cations or polycations chelated by anionic moieties of poly(acrylic) chains should be a substantially exothermic process due to creation of multiple regular anion to cation bonds neutralizing their respective electric charges. Nevertheless, the present inventors found that the aforementioned process is very slow at ambient temperature. Surprisingly at higher temperatures e.g., 90° C.-130° C. the cross-linked poly(acrylic) silver matrix is formed much faster and even remains stable in the solution after cooling to ambient temperature. As a result, the present inventors obtained substantially more effective compositions for creating a robust hemostatic wound covering, compared to the ones described in the prior art (WO 2018/047157). Not less surprisingly, although albumin is present in a lesser concentration in the lymph compared to blood plasma, compositions according to some embodiments of the present teachings may interact with lymph. Thus, these compositions may be used as sealants for stopping postoperative lymphatic leakage (lymphorrhea) and preventing the formations of seromas, which present a significant problem in surgical oncology, abdominal and other fields of surgery.

The haemostatic agent comprised in the used composition is a polyelectrolyte matrix which comprises at least one polymeric carboxylic acid of a predetermined average molecular weight range. The polymeric carboxylic acid is preferably a polymeric α,β-unsaturated carboxylic acid, particularly such as poly (acrylic acid), poly (methacrylic acid) or poly (crotonic acid), with poly (acrylic acid) being particularly preferred. The preparation may comprise a single such as acid, or a mixture of several α,β-unsaturated carboxylic acids.

The concentration of the acid is preferably from about 0.5% to about 5% by weight, particularly from 0.5% to 2% by weight, with a concentration of 1% by weight being particularly preferred.

The wound covering according to the present invention is prepared as the development of haemostatic bactericidal composition described in WO 01/41774 (A1). In compositions containing poly (acrylic acid) as the polymeric matrix, this polyacrylic acid has the structural formula [CH2—CHCO2H]n, where n is at least about 14, particularly from about 14 to about 1400, and preferably from about 14 to about 140. Poly (acrylic acid) having n of about 30 is particularly preferred.

This composition has the bactericidal agent, which is an ionic silver releasing species and is selected from the group consisting of dissolved silver ions, oligomeric silver clusters, silver colloidal nanoparticles and any mixture thereof. The term "ionic silver releasing species" means any species that are capable of releasing silver ions into an aqueous solution containing the aforementioned composition.

Particular ionic silver releasing species are dissolved, free silver ions, Ag+, which may be generated by soluble silver salts, such as silver nitrate or silver acetate, presenting in this water-soluble composition, oligomeric silver clusters, silver colloidal nanoparticles and any mixture thereof. The term "oligomeric silver cluster" as used herein is to be taken to mean substantially oligomeric silver cluster ions, also referred to as coordinate ions, such as $Ag_2^{1+}$, $Ag_4^{2+}$, $Ag_8^{2+}$ and the like. The term "silver nanoparticles" as used herein is to be taken to mean substantially metallic silver nanoparticles, preferably of a size from about 0.5 nm. to about 5 nm. Preferred embodiments of such composition contain from about $1\times10^{-5}$ mole per liter to about 1 mole per liter silver.

The pH of the haemostatic composition used according to this invention is preferably a pH between about 3 and about 10, for example, between about 6 and about 10, and particularly a pH that substantially equal to human blood physiological pH, i.e. about 7.3-7.6.

The haemostatic compositions used herein may be in liquid form, particularly aqueous solutions having long shelf-life. The haemostatic compositions used herein may also be in dry, preferably freeze-dried form, for use by dissolution in pure water before use, to give a liquid preparation. The term "pure water" as used herein means distilled, deionized or otherwise purified water, which may be sterilized, and is physiologically compatible. The freeze-dried compositions may be stored over prolonged periods of time.

The liquid as well as dried compositions may be incorporated in bandages or the like, or applied directly to a wound or to body tissue. The possibility of directly applying the compositions as used herein to wounds and body tissues, for example, during operation, is one of their major advantages.

As described above, the compositions as used herein preferably comprise poly (acrylic acid) as the haemostatic agent, and silver ion releasing material as the bactericidal agent. Thus, the silver may be in a variety of forms including ions, oligomeric clusters and nanoparticles. The poly (acrylic acid) binds with the silver, has a stabilizing effect on the silver and prevents its precipitation. In some embodiments, the poly (acrylic acid) will trap the silver at the blood clot, slowly releasing silver ions, to provide long term, controlled antibacterial effect. This stabilizing effect confers long shelf life to the haemostatic, antibacterial compositions of the invention, which is another major advantage.

According to the second embodiment of the present invention, the polyacrylic matrix structure comprises silver polyacrylate in very small amounts, comparable to natural blood coagulation factors. In this case, the polyacrylic matrix structure serves as the main organizer (plasticizer) of a stable blood clot on the wound surface. That is silver polyacrylate acts as an artificial non-specific blood clotting factor-plasticizer.

According to the third embodiment of the present invention, the medical wound covering means used herein may also be in spray form and can be prepared on the basis of haemostatic composition having combined antibacterial and haemostatic properties, which have storage stability and long shelf-life. The deposition of the composition is preferably achieved by application of its fluid or liquid form onto the surface of the wound, for example, by ultrasonic spray technology.

It follows that a fluid or liquid form of haemostatic composition may be any liquid or gaseous composition, and covers any solution, suspension and emulsion. In this embodiment, the fluid or liquid composition is a particulate composition, which may be liquid, gaseous or dry. This composition may be employed if the size of the particles does not exceed the diameter of the ultrasonic spray nozzle from which the composition exits.

Ultrasonic spray technology comprises use of ultrasonic nozzle systems for application of thin film coatings onto the wound according to the present invention. Advantages of using ultrasonic nozzle systems for coating of the wound include dramatic reduction in overspray, savings in raw materials, water and energy usage, improved process and transfer efficiency, greater uniformity and reduced emissions. Ultrasonic spray systems use high frequency sound vibrations and the nozzles atomize liquids to form a soft spray of micron-sized droplets.

In this proposal, the most preferred source of spray appears pressureless, ultrasonic atomizing nozzles with a soft, low-velocity spray, typically on the order of 75-125 mm per second. These spray delivery means significantly reduces the amount of overspray since the drops tend to settle on the substrate, rather than bouncing off it. This translates into substantial material savings and reduction in emissions into the environment. The spray can be controlled and shaped precisely by entraining the slow-moving spray in an ancillary air stream.

Since the ultrasonic atomization process does not rely on pressure, the amount of liquid atomized by a nozzle per unit time is primarily controlled by the liquid delivery system used in conjunction with a nozzle. The flow rate range for the used ultrasonic nozzles is as low as from a few microliters per second.

Depending on the specific nozzle and the type of liquid delivery system employed, the technology is capable of providing an extraordinary variety of flow and spray possibilities. The liquid delivery system employed can be selected from the group consisting of one or more gear pumps, one or more syringe pumps, one or more pressurized reservoirs, one or more peristaltic pumps, and one or more gravity feeds.

In general, the drops produced by ultrasonic nozzles have a relatively narrow size distribution. In one embodiment the median drop sizes range from 18-68 microns (μm), depending on the operating frequency of the specific type of the nozzle. As an example, for a nozzle with a median drop size diameter of approximately 40 microns, 99.9% of the drops will fall up to the 5-200 micron diameter range. Every ultrasonic nozzle operates at a specific resonant frequency, which is determined primarily by the length of the nozzle. The nozzle has a cone-shaped atomizing surface. Its purpose is to spread out the spray. Some applications require the spray to be very narrow. In those cases, the atomizing surface is sculptured into a flat or nearly-flat surface. Depending on the width requirements of the spray pattern and the required flow rate, the atomizing surface may have a very small diameter or an extended flat section. Drop size in an ultrasonically produced spray can be governed by the frequency at which the nozzle vibrates, and/or by the surface tension and/or density of the liquid being atomized. However, frequency is often the predominant factor. Thus, the higher the frequency, the smaller the median drop size is.

How It Works

The main idea of this invention is use of water solution to activate ionization, acid-base reactions, and related adhesion of compositions to mammalian tissue for hemostasis and/or tissue protection. It is known that viscosities of aqueous polyacrylic acid dispersions are increased by alkaline neutralization. This idea was initially applied to development of topical skin protectants, then to protective sealing of denuded wounds. The original idea was extended with the thought that artificial clotting of blood might result from ionization of the haemostatic components by the water in blood or serum. It was found that water solution, in blood or other leaking body fluids, activates ionization, acid-base reactions and related adhesion of compositions to mammalian tissue for hemostasis and/or tissue protection.

Each application of the methods of this invention makes use of at least one polymeric carboxylic acid in a formulation optimized for the application. However, the polyacrylic acids known as carbomers or carboxypolymethylenes are preferable components. Furthermore, different carbomers are preferred for different applications and usage, as outlined above. Additionally, although non-polymeric components are critical for some applications or usages, ratios of polymeric and non-polymeric components are specific application. The polyacrylic acids may be of various chain lengths and modified monomer components, and have different cross-links as long as they have the monomeric chemical structure [CH2—CHCO2H]n, where n is at least about 14, preferably is about 30. The polyacrylic matrix contains the polyacrylic acid, which has the structural formula [CH2—CHCO2H]n, where n is from about 14 to about 1400, preferably from about 14 to about 140.

Polyacrylic acid (also known as carboxypolymethylene) may be presented as a homopolymer in a family of acrylic acid derivatives known as carbomers. Their polyacrylic acid strands may be cross-linked to various degrees with groups such as allyl sucrose. Such carbomers actively absorb water, melt (without dissolving) at body temperatures, then swell. With water, they constitute a stiff mucilage that is biologically inert but adherent to wet tissue, thereby forming a clot-like wound sealant effective on mammalian tissue (human or non-human) with hemorrhage from trauma or defective blood clotting (from hemophilia or use of anticoagulant medications such as Coumadin).

When the composition includes polyacrylic acid admixed with desiccated water-soluble organic or inorganic base, the acid moiety is neutralized to greater or lesser degree when the composition acquires enough water to support ionic interactions that form salts. Such neutralization, from about pH 4 to pH 8, is known to increase mucilage viscosity in aqueous dispersions.

Medical means "Hemoblok" as used in the present invention, is a local hemostatic. It includes part-time silver salt of polyacrylic acid containing silver nanoparticles. This causes a pronounced bactericidal and bacteriostatic effect of Hemoblok. The hemostatic effect is achieved within 1-2 minutes due to formation by Hemoblok of clot with plasma proteins (mainly albumin).

Recent studies have shown that the action mechanism of Hemoblok does not depend from concentration protein shelter clotting factors in the blood plasma, but depends mainly on the albumin content. Apply Hemoblok composition externally for parenchymal and capillary blood flow. This moistened sterile cotton or gauze pads are applied for the stoppage of bleeding and drying of the wound surface. For large wound surfaces Hemoblok is used as a spray.

In the first stage of the Hemoblok composition use there is developed polyacrylic matrix structure containing albumin molecules in the cells of the polyacrylic matrix. This structure is the primary and during its existence is small, since polyacrylate-anion does not establish a strong connection with the proteins' functional groups and is held only by weak interactions. However, this structure is the primary organizer of the stable film.

Figure 2:
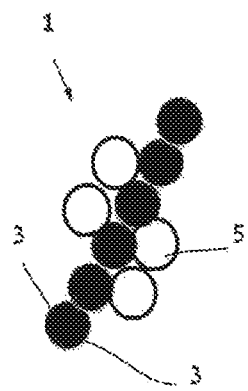
Figure 3A:
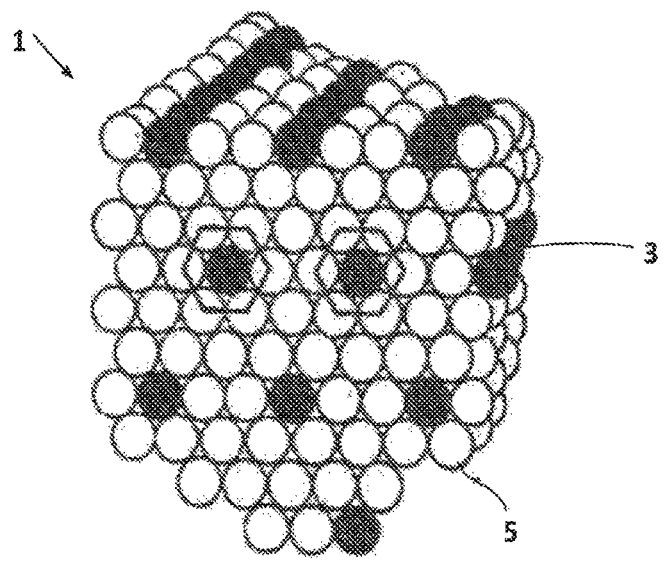
FIGS. 3A-B illustrate the structure of conglomerates of particles, which is formed as a hexagonal packing of polyacrylic matrix.
Figure 3B:
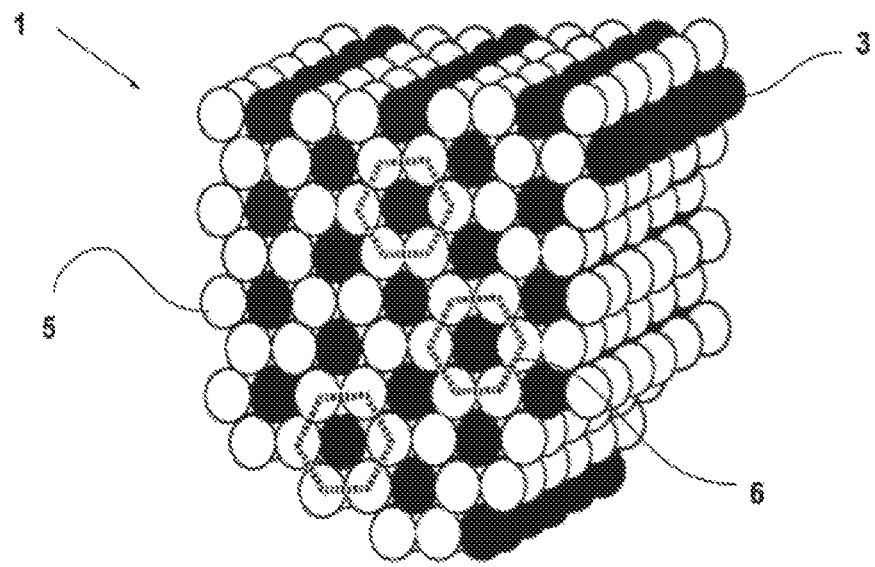

A schematic two-dimensional representation of silver ion cross-linked poly(acrylic) net-like structure is shown in FIG. 1. Silver cations and polycations are chelated by negatively charged dissociated carboxylic groups of the poly(acrylic) chains, thus creating coordination bonded cross-links. The rod-like particles 3 of polyacrylic matrix 1 wherein become centers of proteins' functional groups 5 binding which are adsorbed on the surface of the charged rod-like particles 3 (see. FIGS. 1 and 2). Simultaneously there can occur sorption of proteins' functional groups 5 by side surfaces of charged rod-like particles 3 of polyacrylate anion (FIG. 2). It can be assumed that the structure of such conglomerates of particles are formed by the circuit shown in FIG. 3A and leads ultimately to a hexagonal packing of polyacrylic matrix 1. FIG. 3B illustrates the structure of conglomerates of particles, which is formed as a hexagonal packing of polyacrylic matrix. The hexagonal packing of the rod-like poly(acrylic) matrix particles is shown in black and blood plasma proteins (mainly albumin) is shown in white.

Figure 4:
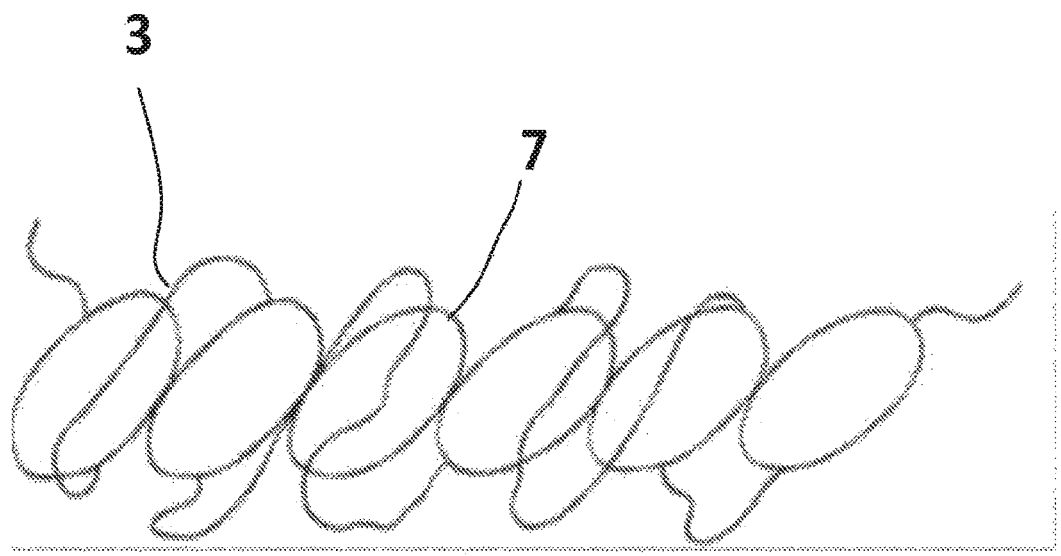
FIG. 4 illustrates the complexes of polyacrylic matrix, which are joined together, forming a loop connected by straight portions.

The viscosity of the solution of thus forming complexes quite sharply increases with degree of polyacrylate anions polymerization. At the same time, sedimentation coefficient remains virtually unchanged. Such a relationship between these hydrodynamic parameters is possible only if the number of particles sufficiently elongated during their elongation. Assuming that the average length of the polyacrylate portion anion to be bounded by protein, is about $8 \times 10^{-8}$ m and significantly is greater than the diameter of the forming complex. It can be assumed that these complexes are somehow joined together, forming a loop connected by straight portions (FIG. 4).

Excess ionized groups, such as adjacent to the surface of the rod-like particles 3 of polyacrylic matrix 1 and located in loops 7 (FIG. 4) creating a hydrophilic zone extended along the surface of rod-like particles 3 promotes the retention of the protein particles in solution. The existence of the loops in the complexes is not dependent on the system viscosity as its water dilution, but is due to viscous electric effect associated with a "swelling" of free areas. In this unfinished revolution loop may be completed by another polyacrylate-anion and asymmetrical chain of protein globules in suitable conditions can be stabilized by relatively short polyacrylate anions rods, the length of which even are smaller than the diameter of the resulting complexes.

Figure 5:
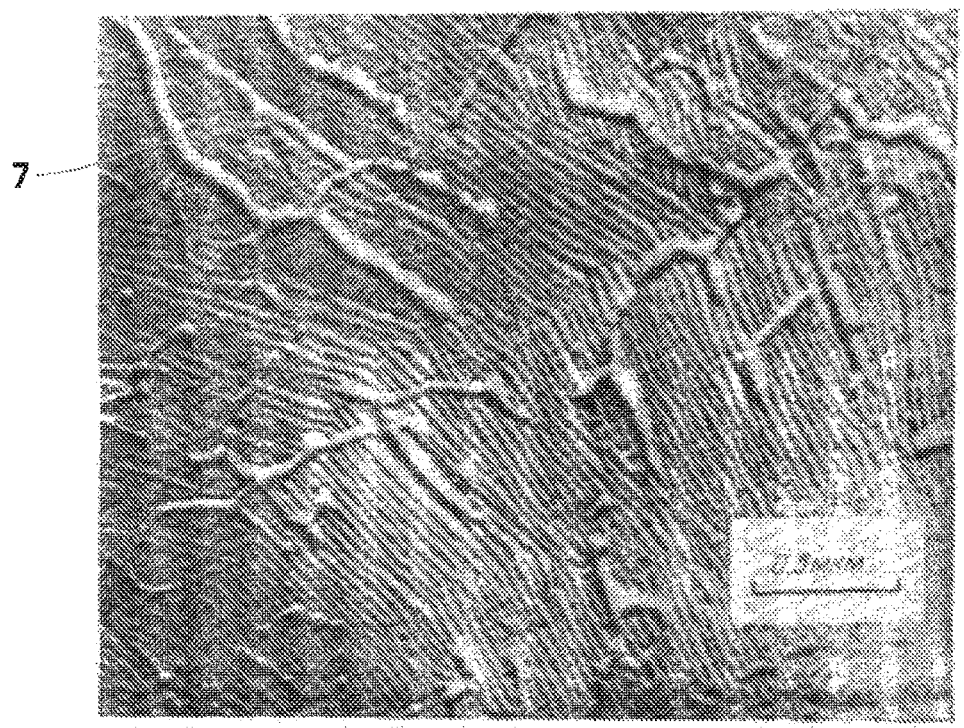
FIG. 5 illustrates proposed structure of the complexes scheme confirmed by electron microscopy.

The above proposed structure of the complex scheme is confirmed by electron microscopy (see. FIG. 5), which is a micrograph of the complex. In the picture there are clearly visible elongated linear formations consisting of linked to each other particles. The thickness of each of the linear formation is about $1 \times 10^{-8}$ meters. Such complexes apparently are formed from polyacrylic acids and proteins by self-organization.

The principle laid down by nature as the basis of Hemoblok building on the surface of the wound polyacrylic matrix structure containing albumin molecules in the cells of the polyacrylic matrix (grid) and is the primary organizer of sustainable polyacrylic film, apparently, is very general and its implementation needs to comply with two hydrodynamic conditions: 1) adhesion protein globules possible to open chain linear polyacrylate-anions, and 2) a sufficiently strong interaction of the adsorbed protein globules (functional groups) and complexes in general. Further feeding Hemoblok onto open wound surface leads to the formation thereon of the multilayer solid polymethacrylic film.

As shown in FIGS. 6-9, the composition can be used in different embodiments of application.

Figure 6:
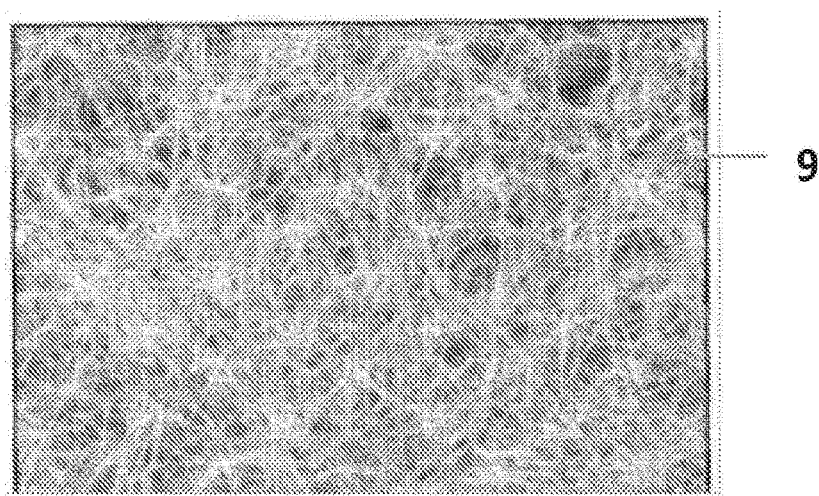
FIG. 6 illustrates a woven or non-woven fabric with applied haemostatic composition.

In the first embodiment of the invention, a composition as described above can be applied to a woven or non-woven fabric material 9, which is selected from the group consisting of gauze, paper, plastics, silicone polymers, resorbable materials, latexes and suitable derivatives of thereof (see. FIG. 6). At the same time this resorbable material is selected from the group consisting of proteinaceous materials, carbohydrate substances and resorbable suture materials.

Woven or non-woven material 9 impregnated or coated with the above composition is applied to the open surface of the wound and serves to protect it from further damage. Such damage may occur from a loss of substances by the body (such as water, blood, plasma, serum, proteins, electrolytes, nutrients), as well as for protection of the wound surface from access and further damage by conventional environmental substances (such as oxygen, dirt, foreign antigens proteins, pathogens, etc.). Wound covering with haemostatic composition in this embodiment secures the open surface of the wound and, accordingly, it is associated with ions physiologically balanced electrolytes to provide a physiological osmotic interaction and pH properties.

In the second embodiment (not shown in the drawings), the polyacrylic matrix structure comprises silver polyacrylate in very small amounts, comparable to natural blood coagulation factors. In this case the polyacrylic matrix structure serves as the main organizer (plasticizer) of stable blood clot on the wound surface. That is silver polyacrylate acts as an artificial non-specific blood clotting factor-plasticizer.

Figure 7:
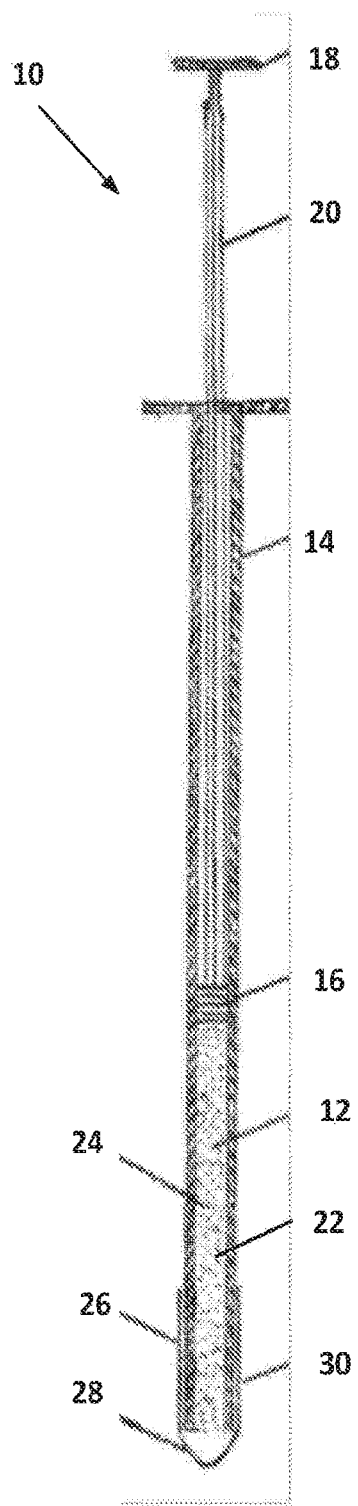
FIG. 7 illustrates a syringe type device for haemostatic composition applying.

In the third embodiment, as shown in FIG. 7, the composition may be delivered to the open surface of the wound by using syringe type device 10. This hemostatic composition 12 may be pre-loaded into barrel 14 of syringe 10 and extruded therefrom by pressing on handle 18 of stock 20. When there are any options of haemostatic composition, which needs not be premixed before application to the open wound, the delivery can be achieved by several parallel arranged barrels 14 of syringe 10 (not shown).

A preferred embodiment of apparatus 10 is shown in FIG. 7. Device 10 includes barrel 14, which internal cavity 22 may be divided into separate sealed compartments for storage of composition 12, labeled as first storage compartment 24 and second storage compartment 26. Compartments 24 and 26 are sealed relative to one another during storage so that composition 12 in storage compartment 24 will not contact or otherwise interact with the composition in another storage compartment 26.

Seals (not shown) are located within storage compartments 24 and 26 for composition 12 and serves to create a dynamic seal with the inner walls of compartments 24 and 26, so that when components of composition 12 are stored in compartments 24 and 26, there is no leakage through these seals. Thus, when piston 16 moves in a sliding motion within barrel 14 toward distal end 28 of this barrel 14, any components of composition 12 in compartments 24 and 26 are forcedly transported within said barrel 14 towards its distal end 28. Usually barrel 10 is equipped with a cap (not shown) for storage, and tip 30 is installed immediately before use of syringe 10.

Figure 8:
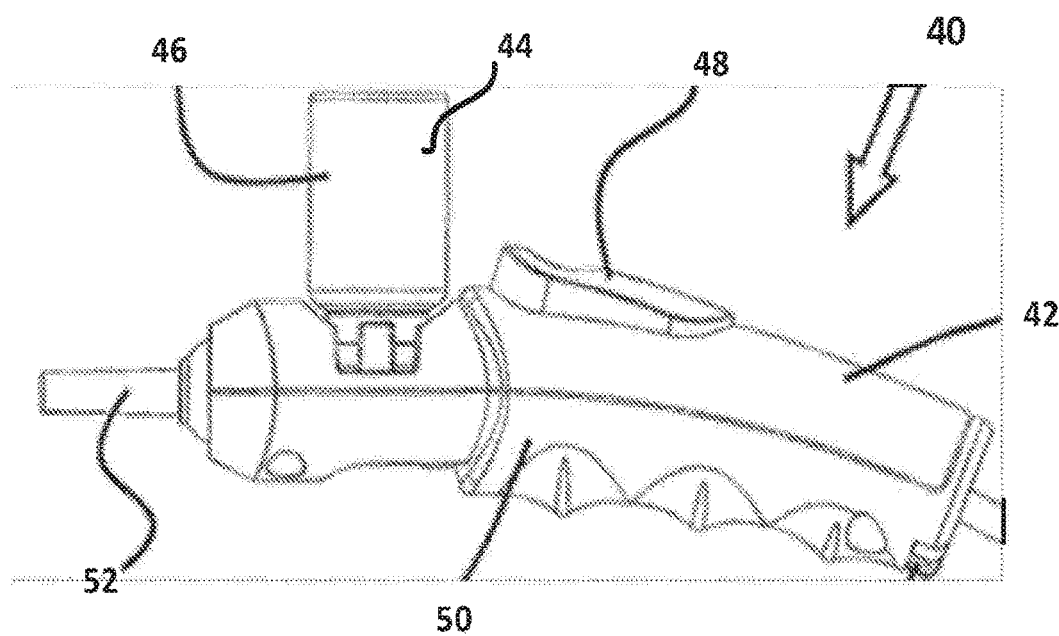
FIG. 8-9 illustrate another device for haemostatic composition applying which is in the form of mechanical or pneumatic gun.
Figure 9:
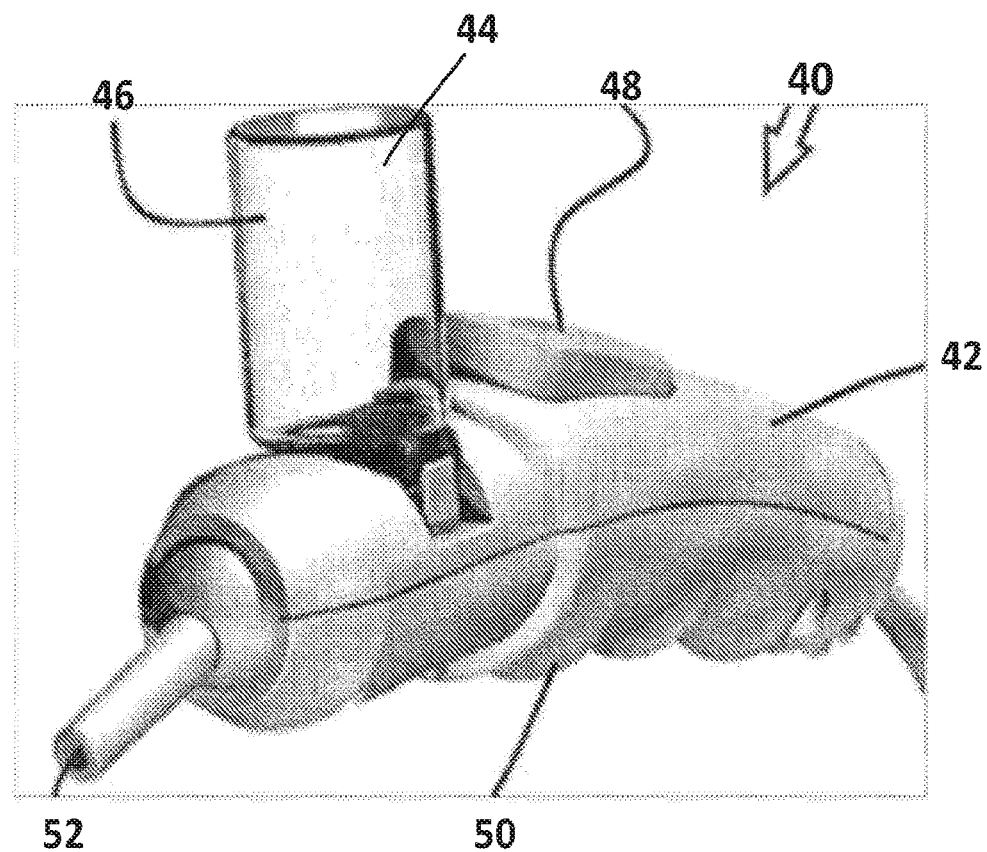

In the third embodiment, as shown in FIGS. 8 and 9, the composition may be delivered to the open surface of the wound using device 40. Device 40 may be in the form of mechanical or pneumatic gun 42 with composition 44 pre-loaded into chamber 46 of this gun 42. Upon manual actuation of control button 48 of gun 42 handle 50, composition 44 is forcibly ejected from distal end 52 of gun 42. Gun 42 can be equipped with a removable dilator (not shown in the drawings) at its distal end 52, which facilitates application of composition 44 in deep and/or on wide wounds.

EXAMPLES

To determine the safety and effectiveness in achieving hemostasis in actively bleeding tissues influenced Hemoblok hemostatic composition for abdominal laparoscopic surgery, the laboratory and clinical studies have been conducted.

On the first stage there were held the laboratory studies on animals (dogs). We determined the safety and efficiency of the hemostatic composition Hemoblok for abdominal surgery and the rate of achieving hemostasis in actively bleeding tissue of the abdominal cavity.

Example 1

Figure 10:
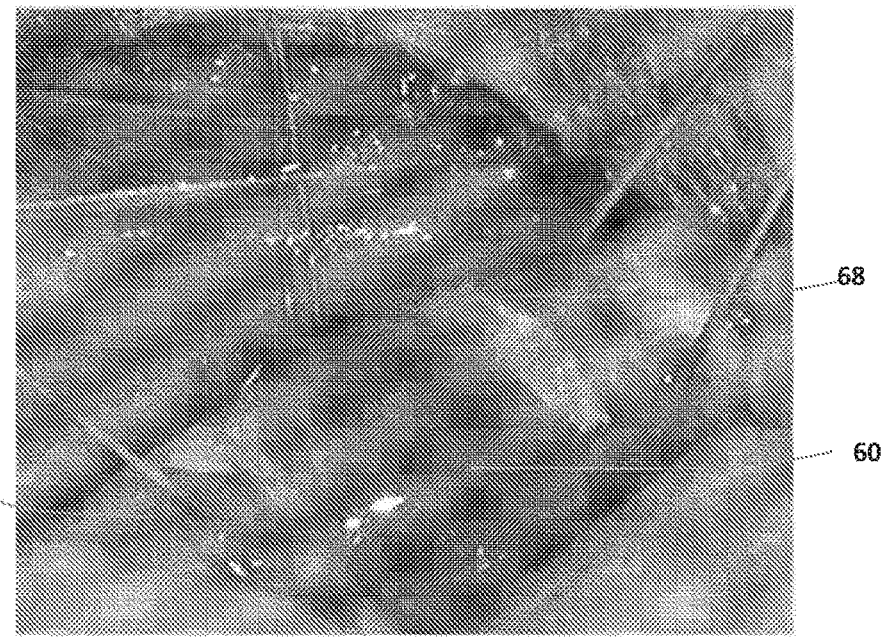
FIG. 10 illustrates a visible anastomosis of aorta prior to the application Hemoblok.
Figure 11:
FIG. 11 illustrates anastomosis of aorta after Hemoblok application.

In the illustrated example of this laboratory study there was carried out at the treatment of aortic anastomosis at mongrel dogs. Hemostasis was occurred within 1.5 minutes (see FIGS. 10, 11). On FIG. 10 is visible anastomosis 60 of aorta 62 prior to the application Hemoblok. On FIG. 11 is seen anastomosis 64 of aorta 62 after application of Hemoblok, wherein the coating is formed as the clot elastic 66. Hemoblok Hemostatic composition in this case was delivered to the wound tissue by gauze napkin 68 impregnated with this composition.

Example 2

Figure 12:
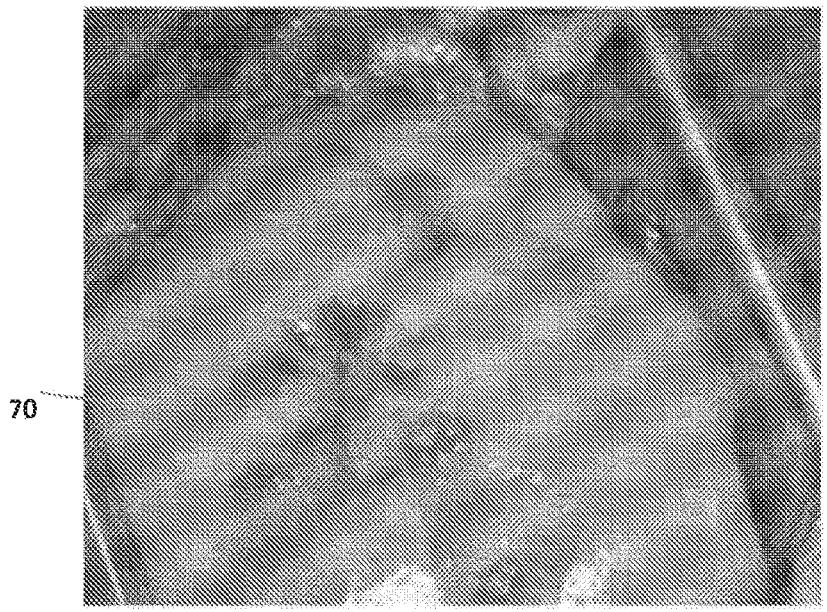
FIG. 12 illustrates using the Hemoblok for hemostasis at wound sewn of the dog lung.
Figure 13:
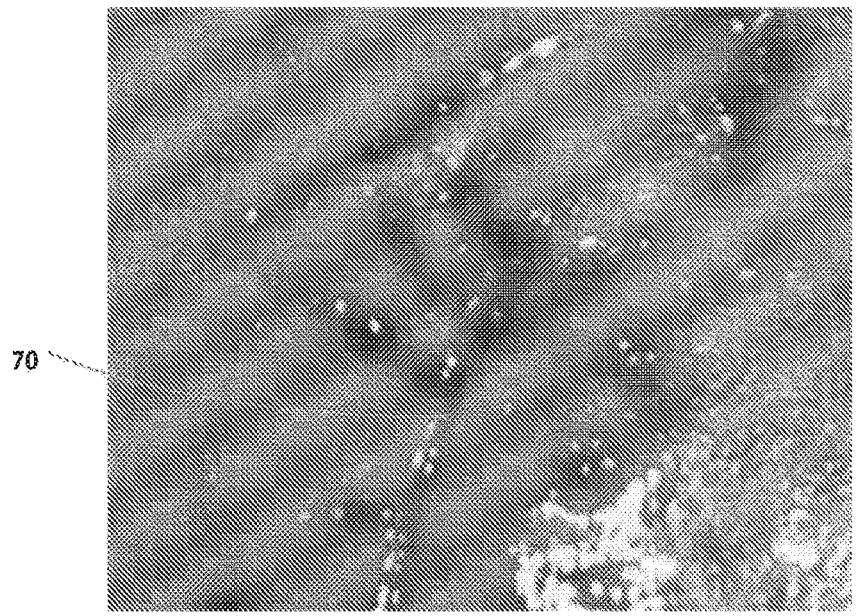
FIG. 13 illustrates surgical suture after applying of Hemoblok composition.

In this case, it was carried out using the Hemoblok for hemostasis at wound sewn of the dog lung (wound depth of 1 cm, 3 cm length) (see FIG. 12). The lung thus performs its physiological function. In FIG. 12 is seen surgical suture 70 wound on the lung. Bleeding was stopped 60 seconds after Hemoblok contact with the wound surface of the dog. In FIG. 13 is visible surgical suture 70 after applying of Hemoblok composition. Delivery of the composition to the surface of the wound was carried out using a device such as a syringe 10.

Example 3

The clinical studies were further conducted at human volunteers. The studies were conducted in Russia on the basis of the Department of Surgery at Municipal Clinical in the city of Kazan. The study including 26 patients were performed at the department of surgery. The purpose of research is clinical evaluation of safety and effectiveness in achieving hemostasis in actively bleeding tissue of the abdominal cavity under the influence Hemoblok composition for abdominal and laparoscopic surgery.

The composition was used to diffuse (capillary) bleeding from the liver and dissected plane viscero-visceral and viscero-parietal adhesions in patients during surgical interventions for acute surgical pathology.

The hemostatic effect was evaluated immediately after application (next 5 min) Hemoblok composition and 24 hours after the surgery. The etiology of diseases, which required surgery: acute destructive calculous cholecystitis −11 (42.3%), acute adhesive intestinal obstruction −15 (57.7%) cases. Depending on the method of delivery of a haemostatic Hemoblok composition on the bleeding surface to form a wound covering all the observed patients were divided into two groups.

The first group included 11 patients who underwent endovideolaparoscopic cholecystectomy for acute calculous cholecystitis. Hemoblok was applied to the bleeding surface of the bed remote gallbladder through richly moistened (25 ml of the product) small gauze napkin. The last delivered to the wound surface through 5-mm. laparoscopic port.

The second group included 15 patients with acute surgical pathology of abdominal organs, operated through the open method of laparotomy. Hemoblok was applied to an open wound surface by copiously moistened gauze napkin. Surgical treatment for acute destructive cholecystitis in all cases were performed by endovideolaparoscopic cholecystectomy. During the surgery all patients in this group occurred diffuse (capillary) bleeding from the gallbladder bed remote. During the operation, there was used coagulation, thus, artificially created by coagulation necrosis area increased postoperative risk of infectious complications. That is why another attractive aspect of the Hemoblok application was its antibacterial effect.

Surgical treatment for acute adhesive intestinal obstruction in all cases were carried out by open laparotomy, viscerolise. During operations in all patients in this group occurred diffuse (capillary) bleeding from a plurality of planar adhesions dissected. Excessive coagulation of serous cover, unfortunately, did not provide adequate haemostatic effect, as well as in the first group of patients.

Figure 14:
FIG. 14 shows diffuse bleeding during liver biopsy.
Figure 15:
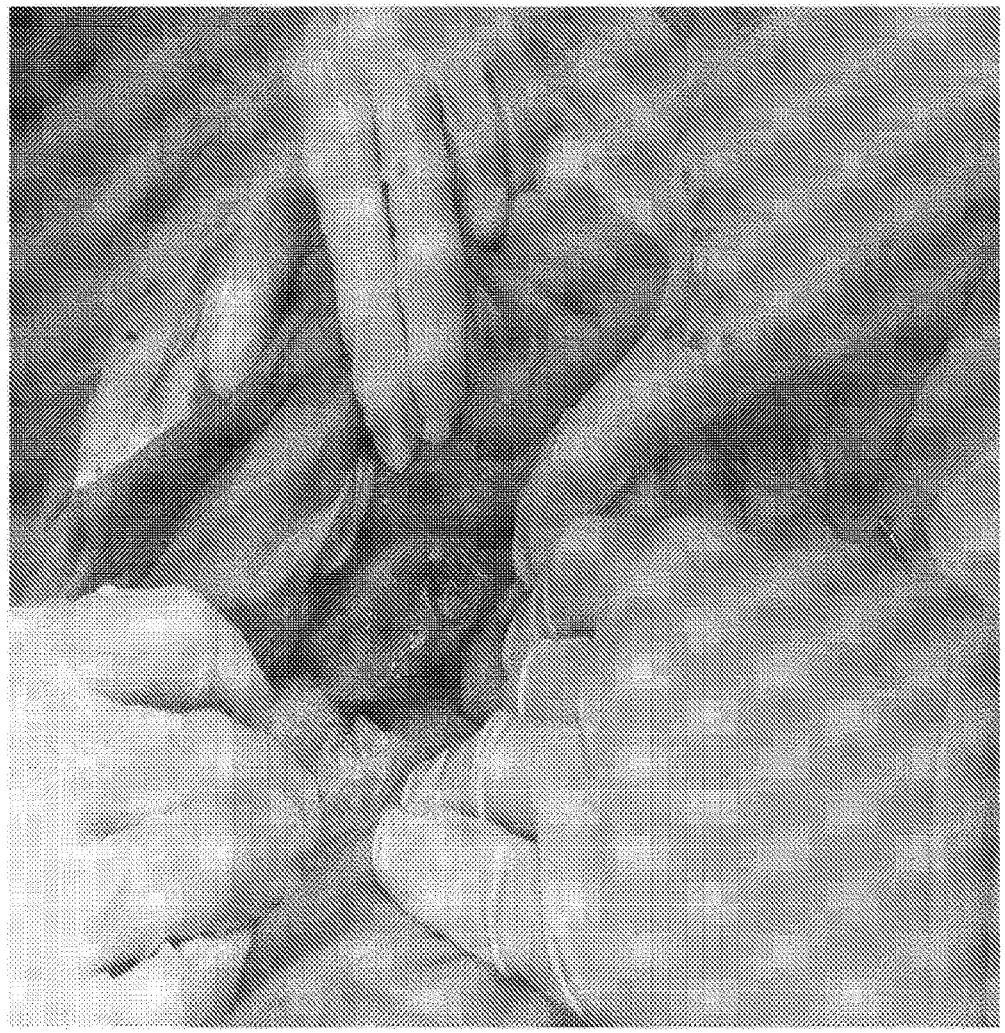
FIG. 15 shows the bleeding stopped by wound coated formed with Hemoblok composition.

In open surgery gauze napkin was moistened with an average of 25-50 ml Hemoblok composition, while the most difficult laparotomy a big gauze napkin was moistened by 100 ml. of composition. Before using these napkins on the bleeding surface a short pre-imposed a dry cloth were used. After its removal immediately was imposed napkin moistened with the Hemoblok composition. The exposition was 2-3 min. In all cases, stable hemostasis (see. FIGS. 14, 15) has been reached. In FIG. 14 shows diffuse bleeding during liver biopsy. In FIG. 15 shows how the bleeding was stopped by wound coated formed by Hemoblok composition.

In 23 (88.5%) cases out of 26 was obtained stable hemostatic effect. The mean time of hemostasis was 2.09±0.2 and 2.53±0.15 minutes in the first and second groups of patients, respectively. In the first group of patients hemostasis was stopped for 1-3 minutes at 10 (90.9%) of 11 patients. This secondary bleeding and suppuration have not been fixed. At 1 (9.1%) patient in the first group there was a recurrence of the bleeding gallbladder bed remote, requiring repeat surgery (see. Table 1).

TABLE 1

Hemostatic effect of Hemoblok during endovideolaproskopic cholecystectomy

| ## | Bleeding surface, cm² | Pronounced bleeding | The amount of Hemoblok, ml | Final stop time of bleeding, min | Blood loss up complete hemostasis, ml |
|---|---|---|---|---|---|
| 1 | 8.75 | + | 25 | 2.5 | 110 |
| 2 | 8.5 | + | 25 | 3 | 80 |
| 3 | 8.25 | + | 25 | 1 | 65 |
| 4 | 8 | + | 25 | 2 | 75 |
| 5 | 7.5 | + | 25 | 2 | 90 |
| 6 | 6.5 | + | 25 | 1.5 | 85 |
| 7 | 6.25 | + | 25 | 2.5 | 95 |
| 8 | 7.5 | + | 25 | 2 | 75 |
| 9 | 7.6 | + | 25 | 3 | 110 |
| 10 | 8.5 | + | 25 | 2 | 100 |
| 11 | 9.5 | + | 25 | 1.5 | 70 |
| Total | 7.86 ± 1.1 | + | 25 | 2.09 ± 0.2 | 86.81 ± 11.5 |

In the second group of patients, 13 (86.7%) at the 15 patients there came hemostasis for 1-3 minutes. Secondary bleeding was not recorded. At 2 (13.3%) patients of the second group re-bleeding arose, requiring additional re-use of the Hemoblok composition with an exhibition of 4 minutes, so the total time of hemostasis in these patients was 6 minutes (Table. 2).

TABLE 2

Hemostatic effect of Hemoblok during open laparotomy

| ## | Bleeding surface, cm² | Pronounced bleeding | The amount of Hemoblok, ml | Final stop time of bleeding, min | Blood loss up complete hemostasis, ml |
|---|---|---|---|---|---|
| 1 | 18.5 | + | 100 | 2 | 250 |
| 2 | 18.5 | + | 100 | 1.5 | 280 |
| 3 | 18.5 | + | 100 | 2 | 180 |
| 4 | 10 | + | 100 | 2 | 175 |
| 5 | 15.5 | + | 100 | 2 | 290 |
| 6 | 16.5 | + | 100 | 2.5 | 185 |
| 7 | 18.5 | + | 100 | 1.5 | 190 |
| 8 | 25.5 | + | 100 | 1 | 300 |
| 9 | 17.5 | + | 100 | 2 | 250 |
| 10 | 22.5 | + | 100 | 6 | 300 |
| 11 | 19.5 | + | 100 | 2.5 | 270 |
| 12 | 20 | + | 100 | 3 | 280 |
| 13 | 21 | + | 100 | 2 | 250 |
| 14 | 22 | + | 100 | 6 | 290 |
| 15 | 15.5 | + | 100 | 2 | 270 |
| Total | 18.43 ± 2.3 | + | 100 | 2.53 ± 0.15 | 250.7 ± 7.5 |

Thus, recurrent bleeding in both groups were observed at 3 patients (11.5%) patients. In all 3 cases, there were systemic violations of blood coagulation. No clinically significant adverse reactions associated with the use Hemoblok composition were observed. Conducted clinical analysis of the results of applying the composition to form Hemoblok protective wound coverings in surgical practice was attributed to its clinical advantages of the following aspects:

Wound coverage with Hemoblok is an effective means for stopping diffuse (capillary) bleeding at various kinds of surgeries.

Wound coverage using Hemoblok has antibacterial effects on the wound surface. Wound healing takes place without the use of antibiotics and other antibacterial agents.

Called rapid hemostasis takes from 2.09±0.2 and up to 2.53±0.15 m. This blood loss was 86.81±11.5 and 250.7±7.5 ml at endovideolaparoscopic and open transactions respectively.

In the process of applying of the Hemoblok composition was not observed postoperative complications as fistula, adhesion formation and the emergence of reactive effusions in the peritoneal cavity.

In the near and distant postoperative, there were not any toxic and allergic reactions, irritation to the surrounding tissue and influence hemostasis in the general circulation.

Wound coverage with Hemoblok compositions is easy to use, equally closes all irregularities on bleeding wound surfaces.

Several examples of a chemical preparations containing compositions according to some embodiments of the above teachings are given below:

Example 4

A powder of poly(acrylic acid) of the average molecular mass of approximately 2,000 is dissolved in pure water so that its concentration is 1.10% by weight. Then 60 μL of 1M AgNO3 solution were added to 10 mL of the aforementioned poly (acrylic acid) solution. The pH of the solution was adjusted to 7.2 using saturated KOH solution in water. The solution is poured into glass vials and sealed. The vials are placed into sterilization autoclave and heated to 125° C. (257° F.) at increased pressure (approximately 2 atmospheres) during 30-40 min and subsequently allowed to cool to ambient temperature.

Example 5

A volume of 30 μL of 1M silver acetate solution is added to 10 mL of 5 mM solution of poly(acrylic acid) of an average molecular weight of approximately 5,000. The solution pH is neutralized by adding saturated aqueous KOH. The solution is poured into glass vials and sealed. The vials are placed into sterilization autoclave and heated to 120° C. (248° F.) at increased pressure (approximately 2 atmospheres) during 30-40 min and subsequently allowed to cool to ambient temperature.

Example 6

Poly(acrylic acid) (15 g) having an average molecular weight of approximately 8,000 was dissolved in 1 L of water and left to stand for 24 hours. The solution pH was adjusted to 7.4 by the addition of solid sodium hydroxide. A quantity of 1 g of silver nitrate was gradually added to a continuously stirred solution of poly (acrylic acid). Once a clear solution was obtained, it was transferred into glass vials which were then sealed. The vials were placed into sterilization autoclave and heated to 125° C. (257° F.) at increased pressure (approximately 2 atmospheres) during 30-40 min and then subsequently allowed to cool to ambient temperature.

CONCLUSIONS

1. Wound coverage with Hemoblok is a sufficiently effective local hemostatic.
2. The hemostatic effect does not depend on the method of the Hemoblok composition delivery to a bleeding wound surface and manifests itself in open laparotomy, using endovideolaparoscopic technologies, etc.
3. During endovideolaparoscopic interventions efficient haemostatic effect of wound coverings using Hemoblok is evident in 90.9% of cases, and with open laparotomy—in 86.7%.
4. Infectious complications associated with the use of Hemoblok composition were not observed.

5. The Hemoblok can be used as an adjuvant treatment facility to deal with parenchymal bleeding during abdominal and laparoscopic surgery. Hemoblok Hemostatic composition is sufficiently effective local hemostatic.

The wound covering on the base of Hemoblok hemostatic composition can also be provided as a spray or aerosol that can be directly applied to a wound. The applicators such as woven or non-woven fabric 9, syringe 10, or gun 42 and other suitable applicators can also be provided to allow rescue personal, emergency medical personnel, family members, or others with little or no professional medical training to apply the composition to wounds in emergency situations. The blood clotting composition is particularly useful for medical emergency first responders, police, and military personnel to stop bleeding from wounds in the field.

The hemostatic composition, which typically will be applied to a wound by a first responder at the incident site can include as prophylactic antibiotic selected from antibiotic classes including: penicillin's, penicillin combinations, sulfonamides, as well as other suitable antibiotic compositions and combinations thereof.

The wound covering on the base of Hemoblok compositions and proposed method of the subject invention may be widely useful, for instance, in the following applications:

Preventing hemorrhage or minor bleeding at the site of injury by artificially coagulating blood, adhering the blood or product coagulum, immobilizing damaged tissue to minimize further injury, and preventing further contamination of a wound;

Protecting of wounds from possible injury by coating them with semi-permeable barrier films;

Surgical use to accelerate epithelialization of denuded surfaces, preventing excessive formations of connective tissue during wound healing, temporary sealing of the bleeding edges of soft internal organs such as liver, spleen, or lung prior to the application of biodegradable materials by highly skilled surgeons;

Use as a bioadhesive to stabilize damaged tissue as a soft tissue splint, coat and seal raw surfaces such as blister bases, abrasions or burns;

Use as a means for delivery of drugs to or through wounded surfaces.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The invention claimed is:

1. A method for preparing a water-soluble sealant composition comprising the step of:
adding soluble silver salt to a polyacrylic acid (PAA) solution;
adjusting the pH of said PAA solution to 7-7.4; and
heating said PAA solution to 90-125 20 C.,
wherein said PAA has a molecular weight of 1000-8000, and wherein said composition comprises a cross-linked poly(acrylic) silver matrix having an affinity to proteins.

2. The method of claim 1, wherein said silver salt selected from the group consisting of silver nitrate and silver acetate and combinations thereof.

3. The method of claim 1, wherein said matrix is capable of creating hydrophilic zones which bind said proteins.

4. The method of claim 1, wherein said composition when in contact with proteins, forms hexagonal packing complexes of poly(acrylic) particles and proteins.

5. The method of claim 4, wherein said composition forms a clot made of a multi-layered grid structure.

6. The method of claim 4, wherein said hexagonal packing complexes create loops that form cells comprising said proteins.

7. The method of claim 1, wherein said proteins comprise albumin.

8. The method of claim 1, wherein said proteins are from a body fluid selected from the group
consisting of blood, lymph and combinations thereof.

9. The method of claim 1, comprising the step of preparing the polyacrylic acid (PAA) solution.

10. The method of claim 1, wherein the step of adjusting the pH is done with an alkali selected from the group consisting of NaOH and KOH and combinations thereof.

11. A water-soluble sealant composition prepared by the method of claim 10.

12. The method of claim 1, wherein the step of heating is done above ambient pressure.

13. The method of claim 12, wherein said pressure is 2 atmospheres absolute.

14. The method of claim 1, wherein the step of heating is for more than 30 minutes.

15. The method of claim 14, wherein the step of heating is for up to 40 minutes.

16. The method of claim 1, comprising the step of cooling to ambient temperature after adjusting the pH.

17. A water-soluble sealant composition prepared by the method of claim 1.

18. The composition of claim 17, wherein said composition is applied for stopping leakage of body fluid selected from the group consisting of blood, lymph and combinations thereof.

19. The composition of claim 17, wherein said composition is applied for a medical condition selected from the group consisting of hemorrhage, lymphorrhea and combinations thereof.

* * * * *

UNITED STATES PATENT AND TRADEMARK OFFICE
CERTIFICATE OF CORRECTION

PATENT NO. : 12,090,247 B2
APPLICATION NO. : 17/157502
DATED : September 17, 2024
INVENTOR(S) : Alexander Plotkin and Dmitri Menglet Page 1 of 1

It is certified that error appears in the above-identified patent and that said Letters Patent is hereby corrected as shown below:

On the Title Page

Item (72):
Please remove Inventor 1 residence "Tel Aviv (IL)" and replace with "Istra (RU)".

Signed and Sealed this
Twenty-second Day of October, 2024

Katherine Kelly Vidal
*Director of the United States Patent and Trademark Office*